US012571791B2

(12) United States Patent
Woo et al.

(10) Patent No.: US 12,571,791 B2
(45) Date of Patent: Mar. 10, 2026

(54) METHODS FOR EVALUATING CARDIAC SAFETY OF DRUG USING CARDIOMYOCYTES DERIVED FROM HUMAN STEM CELLS

(71) Applicant: NEXEL CO., LTD., Seoul (KR)

(72) Inventors: Donghun Woo, Seoul (KR); Jieun An, Seoul (KR); Subin Kim, Seoul (KR); Seulgi Yoon, Seoul (KR); Seunghee Yeon, Seoul (KR); Jinhyuk Chang, Hanam-si (KR)

(73) Assignee: NEXEL CO., LTD., Seoul (KR)

( * ) Notice: Subject to any disclaimer, the term of this patent is extended or adjusted under 35 U.S.C. 154(b) by 452 days.

(21) Appl. No.: 18/015,972

(22) PCT Filed: Mar. 28, 2022

(86) PCT No.: PCT/KR2022/004331
§ 371 (c)(1),
(2) Date: Jan. 13, 2023

(87) PCT Pub. No.: WO2022/239960
PCT Pub. Date: Nov. 17, 2022

(65) Prior Publication Data
US 2023/0296588 A1 Sep. 21, 2023

(30) Foreign Application Priority Data
May 14, 2021 (KR) ........................ 10-2021-0062662

(51) Int. Cl.
*G01N 33/50* (2006.01)
*C12N 5/077* (2010.01)
(52) U.S. Cl.
CPC ....... *G01N 33/5061* (2013.01); *C12N 5/0657* (2013.01); *C12N 2500/38* (2013.01); *C12N 2506/03* (2013.01); *C12N 2533/52* (2013.01)

(58) Field of Classification Search
None
See application file for complete search history.

(56) References Cited

U.S. PATENT DOCUMENTS

2012/0107861 A1* 5/2012 Abrams ............. G01N 33/6887
435/29

FOREIGN PATENT DOCUMENTS

KR 10-1916393 B1 11/2018
KR 10-1994035 B1 6/2019

OTHER PUBLICATIONS

Clements, Mike; "Multielectrode array (MEA) assay for profiling electrophysiological drug effects in human stem cell-derived cardiomyocytes" Current Protocols in Toxicology, Supplement 68, 22.4.1-22.4.32, 2016 (Year: 2016).*

(Continued)

*Primary Examiner* — David W Berke-Schlessel
(74) *Attorney, Agent, or Firm* — Revolution IP, PLLC

(57) ABSTRACT

A method of assessing drug cardiac safety using human stem cell-derived cardiomyocytes, includes: step (A) of preparing cardiomyocytes by culturing human stem cells to differentiate into cardiomyocytes; step (B) of diluting fibronectin in DPBS (Dulbecco's phosphate buffered saline) at a concentration of 50 µg/ml; step (C) of adding the fibronectin solution, obtained by diluting to the concentration of 50 µg/ml in step (B); step (D) of placing the MEA plate; step (E) of removing the fibronectin solution from specific wells of the MEA plate; step (F) of adding a predetermined medium to the specific wells of the MEA plate; and step (G) of measuring changes in information values about beat rate, spike amplitude and field potential duration depending on whether a drug to be assessed has been added to the wells of the MEA plate.

4 Claims, 4 Drawing Sheets

(56) References Cited

OTHER PUBLICATIONS

Sigma-Aldrich; Product Information—Dulbecco's Phosphate Buffered Saline (Year: 2014).*

Nozaki, Yumiko; et al; "CSAHi study: Validation of multi-electrode array systems for prediction of drug-induced proarrhythmia using human iPS cell-derived cardiomyocytes-assessment of inter-facility and cells lot-to-lot-variability" Regulatory Toxicology and Pharmacology, 77, 75-86, 2016 (Year: 2016).*

Office Action of Korean Patent Application No. 10-2021-0062662 mailed Jun. 30, 2023.

G.Navarrete et al., "Screening Adverse Drug-Induced Arrhythmia Events Using Human Induced Pluripotent Stem Cell-Derived Cardiomyocytes and Low-Impedance Microelectrode Arrays", Circulation, Sep. 2023, vol. 128.

International Search Report for PCT/KR2022/004331 mailed Aug. 18, 2022 from Korean Intellectual Property Office.

Sala, L. et al., "Electrophysiological Analysis of human Pluripotent Stem Cell-derived Cardiomyocytes (hPSC-CMs) Using Multi-electrode Arrays (MEAs)", Journal of Visualized Experiments, 2017, vol. 123, thesis No. e55587, pp. 1-15.

Millard, D. C. et al., "The CiPA Microelectrode Array Assay with hSC-Derived Cardiomyocytes: Current Protocol, Future Potential. Stem Cell-Derived Models in Toxicology", 2017, part of the Methods in Pharmacology and Toxicology book series, pp. 83-107.

* cited by examiner

| | | | | |
|---|---|---|---|---|
| DMSO (%) | 0.1 | 0.1 | 0.1 | 0.1 |
| Nifedipine (uM) | 0.001 | 0.01 | 0.1 | 1 |
| E4031 (uM) | 0.003 | 0.01 | 0.03 | 1 |
| Mexiletine (uM) | 1 | 3 | 10 | 30 |

METHODS FOR EVALUATING CARDIAC SAFETY OF DRUG USING CARDIOMYOCYTES DERIVED FROM HUMAN STEM CELLS

TECHNICAL FIELD

The present invention relates to a method of assessing drug cardiac safety using human stem cell-derived cardiomyocytes.

BACKGROUND ART

The QT interval on an electrocardiogram (ECG) is a value representing the duration of depolarization and repolarization. A prolonged QT interval may cause severe tachyarrhythmias such as TdP (Torsades de pointes).

In this regard, hERG assay, which assesses the drug's ability to block human ether-a-go-go related gene (hERG) ion channels, is performed in non-clinical studies to prevent approval of drugs that may cause cardiac arrhythmias upon administration during the new drug development stage.

For continued research and experiments on drug-induced cardiotoxicity using hERG assay, cardiomyocytes derived from human stem cells are used as a clinical source.

The prior art of evaluating drug-induced cardiotoxicity using cardiomyocytes differentiated from human pluripotent stem cells includes Korean Patent No. 10-1916393, titled "In vitro cardiotoxicity testing using human pluripotent stem cell-derived cardiomyocytes" (hereinafter referred to as "conventional art").

However, conventional methods of assessing cardiac safety of a drug using cardiomyocytes, including the conventional art, are based on hERG assay which exhibits high sensitivity and low specificity. Accordingly, these methods focus on one of the various channels involved in the action potential, thus decreasing its correlation to the drug's potential to cause TdP.

More specifically, conventional methods of assessing the cardiac safety of a drug using cardiomyocytes, including the conventional cart, are based on hERG assay and have shown to exhibit a discrepancy of nearly 30% with the results of non-clinical tests for assessing actual risk of arrhythmia. In addition, drugs without cardiotoxicity are subjected to extensive electrocardiographic studies, which further increases its clinical development costs, or drugs that affect QT prolongation, but have little actual TdP risk may be deprived or excluded from further development.

Furthermore, even if these drugs are approved, precautions are inserted on the product label, limiting the clinical use of the drugs, and ultimately lowering their value of the drugs. Therefore, there is a need to present a new paradigm for assessing the potential for TdP. In order to overcome the said problem, a movement to revise the international guidelines for the assessment of the cardiotoxicity of drugs is taking place, with the United States, Japan, and others as the epicenter.

DISCLOSURE

Technical Problem

The present invention has been made in order to solve the problems above, and the objective of the present invention is to provide a method that overcomes shortcomings of the hERG assay currently used for the assessment of the cardiotoxicity of drugs in the preclinical stage of the new drug development and to provide a more accurate and integrated in vitro cardiotoxicity assessment.

Technical Solution

To achieve the above object, a method of assessing drug cardiac safety using human stem cell-derived cardiomyocytes according to the present invention includes: step (A) of preparing cardiomyocytes by culturing human stem cells to differentiate into cardiomyocytes; step (B) of diluting fibronectin in DPBS (Dulbecco's phosphate buffered saline) at a concentration of 50 μg/ml; step (C) of adding the fibronectin solution, obtained by diluting to the concentration of 50 μg/ml in step (B), so as to cover all dots of electrodes disposed in the center of each of a plurality of wells arranged in a multielectrode array (MEA) plate, and adding DPBS to spaces between the wells of the MEA plate to fill the spaces; step (D) of placing the MEA plate, in which the fibronectin solution and DPBS have been added to each well and the spaces between the wells, respectively, in step (C), in a cell incubator maintained at 37° C. under 5% $CO_2$, and subjecting the MEA plate to coating for 50 minutes to 60 minutes; step (E) of removing the fibronectin solution from specific wells of the MEA plate, subjected to coating in step (D), and then seeding the human stem cell-derived cardiomyocytes, prepared in step (A), so as to cover all dots of the electrodes; (F) adding a predetermined medium to each of the specific wells of the MEA plate seeded with the human stem cell-derived cardiomyocytes through step (E), and then incubating the MEA plate in the cell incubator; and step (G) of measuring changes in information values about beat rate, spike amplitude and field potential duration depending on whether a drug to be assessed has been added to each well of the MEA plate, which has been seeded with the human stem cell-derived cardiomyocytes and incubated for a predetermined period of time in step (F), and depending on the addition concentration of the drug, by a multielectrode array (MEA) measurement device electrically connected to the electrodes disposed in each well of the MEA plate, and assessing the cardiac safety of the drug based on the measured information values.

Here, the human stem cells which are differentiated into cardiomyocytes in step (A) are any one cell type selected from among human pluripotent stem cells (hPSCs) and human embryonic stem cells (hPSCs).

In addition, step (B) comprises: step (B-1) of preparing a fibronectin stock by dissolving fibronectin in DPBS at a concentration of 1 mg/ml; and step (B-2) of diluting the fibronectin stock, prepared at a concentration of 1 mg/ml in step (B-1), in DPBS at a concentration of 50 μg/ml.

In addition, step (E) comprises: step (E-1) of adding the human stem cell-derived cardiomyocytes, prepared in step (A), to a plating medium, followed by centrifugation, removing the supernatant, and then adding a fresh plating medium, thereby preparing a cell suspension; and step (E-2) of removing the fibronectin solution from each well of the MEA plate, and then seeding a portion of the cell suspension prepared in step (E-1), which contains 5×10$^4$ human stem cell-derived cardiomyocytes, in each well so as to cover all dots of the electrodes.

Furthermore, step (F) comprises: step (F-1) of subjecting the MEA plate, which has been seeded with a portion of the cell suspension containing the human stem cell-derived cardiomyocytes in step (E-2), to first incubation for 60 minutes; step (F-2) of adding a plating medium to each of the specific wells of the MEA plate subjected to the first incubation in step (F-1), and then placing the MEA plate in a cell incubator maintained at a temperature of 37° C. under 5% $CO_2$, followed by second incubation for 23 hours to 24 hours; and step (F-3) of replacing the plating medium, added to each of the specific wells of the MEA plate subjected to the second incubation in step (F-2), with a maintenance medium, and then placing the MEA plate in a cell incubator maintained at a temperature of 37° C. under 5% $CO_2$, followed by third incubation for 7 days.

Here, step (F-3) is a step of subjecting the MEA plate to the third incubation for 7 days while replacing the maintenance medium, added to each of the specific wells of the MEA plate, with a fresh maintenance medium at 2-day intervals.

Furthermore, step (G) comprises: step (G-1) of replacing the maintenance medium, added to each of the specific wells of the MEA plate subjected to the third incubation in step (F-3), with a fresh maintenance medium, and then placing the MEA plate in a cell incubator maintained at a temperature of 37° C. under 5% $CO_2$, followed by stabilization of the cells for 3 hours to 5 hours; step (G-2) of generating first measurement information by measuring information values about beat rate, spike amplitude and field potential duration for the human stem cell-derived cardiomyocytes, seeded in at least one of the specific wells of the MEA plate subjected to cell stabilization in step (G-1), by the MEA measurement device; step (G-3) of removing a portion of the maintenance medium, which corresponds to $\frac{1}{10}$ of the total volume of the maintenance medium, from at least one of the specific wells of the MEA plate subjected to cell stabilization in step (G-1), and then adding a predetermined concentration of the drug to be assessed in the same amount as the amount of the removed portion of the maintenance medium, and after 30 minutes to 40 minutes, generating second measurement information by measuring information values about beat rate, spike amplitude and field potential duration for the human stem cell-derived cardiomyocytes, seeded in the well to which the drug to be assessed has been added, by the MEA measurement device; and step (G-4) of assessing the cardiac safety of the drug using change patterns in FPDcF (field potential duration corrected by Fridericia's formula) and spike amplitude depending on the concentration of the drug based on the first measurement information and second measurement information generated in step (G-2) and step (G-3), respectively, wherein step (G-3) is a step of generating two or more pieces of second measurement information by being repeated at least twice while changing the concentration of the drug to be assessed.

Advantageous Effects

The present invention has the following effects.

First, the present invention is the first to propose a method capable of assessing the cardiotoxicity of drugs in vitro in an integrated manner based on multielectrode arrays (MEAs), deviating from the conventional hERG assay-based evaluation method.

Second, it is possible to assess drug cardiac safety by measuring and utilizing a much more comprehensive and diverse data parameters compared to that of the conventional art, such as beat rate, spike amplitude and field potential duration for human stem cell-derived cardiomyocytes seeded in the well of a multielectrode array (MEA) plate.

Third, it is possible to assess the drug cardiac safety in an easier and more accurate manner due to the highly efficient safety assessment processing method, and to reduce the use of animals by using human stem cell-derived cardiomyocytes. Furthermore, tests for evaluating the effects of drugs in a long-term exposure is made possible, along with identifying and evaluating potential differences in the electrophysiological effects that may influence the assessment of ventricular arrhythmia risk.

MODE FOR INVENTION

Preferred embodiments of the present invention will be described more in detail with reference to the accompanying figures. Description of already known technical features will be omitted or be described in short for the sake of brevity. <Description of the Drug Cardiac Safety Assessment Using Human Stem Cell-Derived Cardiomyocytes>

Figure 1:
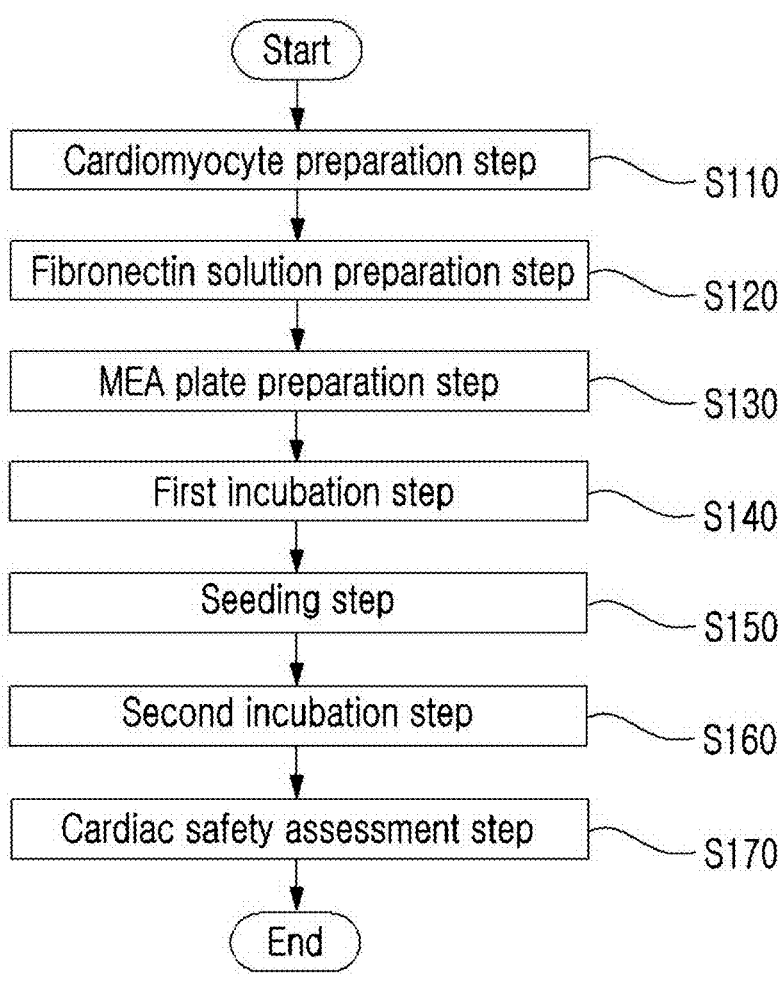
FIG. 1 is a flow chart showing a method of assessing drug cardiac safety using human stem cell-derived cardiomyocytes according to the present invention.

Hereinafter, each step of the method of assessing drug cardiac safety using human stem cell-derived cardiomyocytes according to the present invention will be described in detail with reference to FIG. 1.

(1) Cardiomyocyte Preparation Step <S110, Step (A)>

In this step (S110), the preparation of cardiomyocytes by differentiation of human stem cells is performed.

Here, either one of the human pluripotent stem cells (hPSC) or human embryonic stem cells (hESC) is used to be differentiated into cardiomyocytes according to the predetermined culture process under predetermined culture conditions.

Preferably, using human stem cell-derived cardiomyocytes prepared according to the applicant's previous patent disclosed under Korean Patent No. 10-1994035 (titled "Method of producing functional cardiomyocytes derived from human pluripotent stem cells by cell differentiation and maturation and the human stem cell-derived produced functional cardiomyocytes")

In addition, the produced human stem cell-derived cardiomyocytes may be kept in a liquid nitrogen tank until the seeding step (S150) and may be taken out and thawed before use.

(2) Fibronectin Solution Preparation Step <S120, Step (B)>

In this step (S120), fibronectin is diluted in DPBS (Dulbecco's phosphate buffered saline) to a concentration of 50 μg/ml.

Specifically, the preparation is done in two steps. The fibronectin is prepared in a stock solution with a concentration of 1 mg/ml and is cold stored until use. (Step B-1)

Then using the stock fibronectin solution prepared at 1 mg/ml at step B-1, it is taken out of cold storage and diluted further with DPBS to 50 μg/ml.

(3) MEA Plate Preparation <S130, Step (C)>

In this current step (S13), fibronectin solution diluted to 50 μg/ml in the previous step (S12) is placed on the center of the wells of the MEA plate, ensuring to cover dots of electrodes, and DPBS is added to the space between the wells of the MEA plate.

Figure 2:
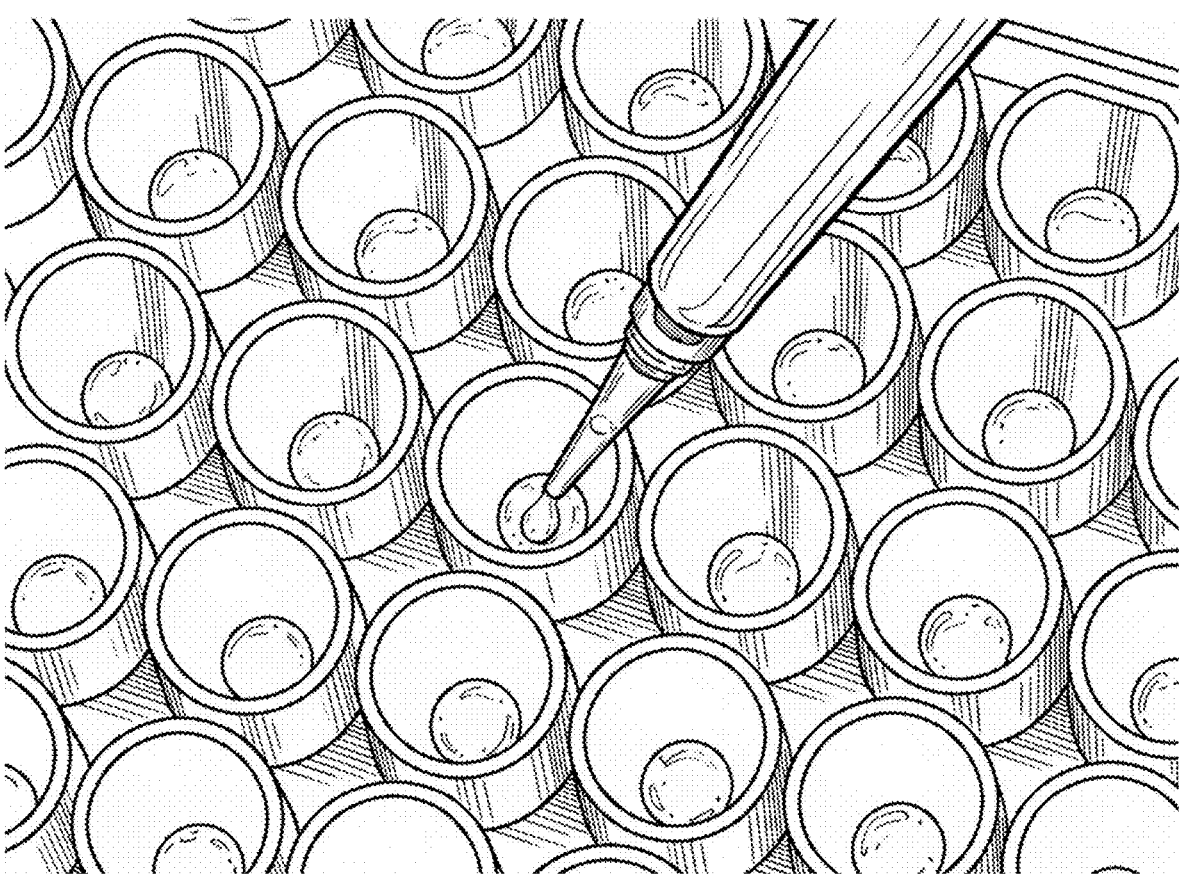
FIG. 2 shows the configuration an MEA plate which is used in an MEA plate preparation step in the method of assessing drug cardiac safety using human stem cell-derived cardiomyocytes according to the present invention.
Figure 3:
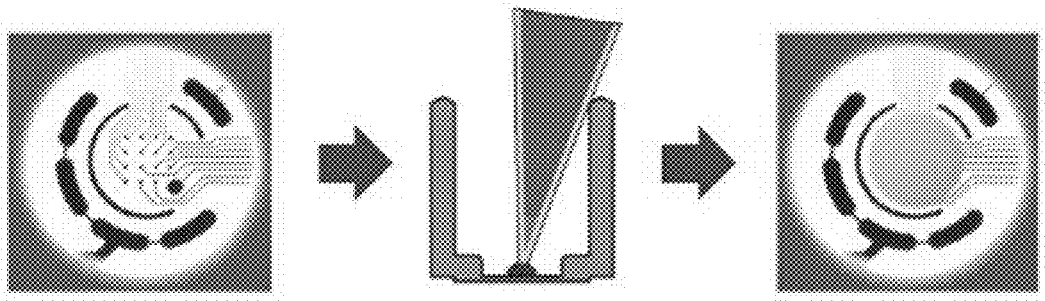
FIGS. 3 and 4 are conceptual views showing a method of adding a substance to or seeding cells in a MEA plate which is used in an MEA plate preparation step in the method of assessing drug cardiac safety using human stem cell-derived cardiomyocytes according to the present invention.

As shown in FIG. 2, the MEA plate is arranged in columns/rows of multiple wells, and in these wells, there are multiple electrodes in form of dots, as can be seen in FIG. 3.

In addition, the MEA measurement device is connected to the dots of the electrodes, which allows it to measure extracellular field potential caused by the microcurrents generated by seeded cardiomyocytes.

Figure 4:
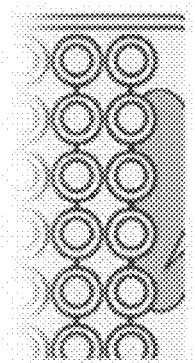

FIG. 3 shows the method of adding 5 μl of the fibronectin solution to the center of the well of the MEA plate in a manner where the solution will cover all dots of the electrode. FIG. 4 shows the method of filling the spaces between the wells of the MEA plate with DPBS to prevent the plate from drying.

(4) First Incubation Step <S140, Step (D)>

In this step (S140), the MEA plate which had fibronectin solution added to the wells and DPBS added to the spaces between the wells in the previous preparation step (S130) is incubated in the cell culture incubator, maintained at 37° C. and 5% $CO_2$ for 50 to 60 minutes.

In specific, the MEA plate is prepared with fibronectin solution added to cover all the electrodes in the wells, and DPBS is added in between the spaces of the wells. And then the MEA plate is placed in the cell culture incubator maintained at 37° C. and 5% $CO_2$ for 60 minutes to ensure thorough coating.

(5) Seeding Step <S150, Step (E)>

In this step (S150), fibronectin solution is removed from the coated plate prepared in the previous step D, then cardiomyocytes prepared in step S110 are seeded onto the surface of the well of the MEA plate, ensuring an even covering of all dots of electrodes.

In specific, the present step is carried out in two steps. First, the human stem cell-derived cardiomyocytes are placed in the plating medium, centrifuged, and aspirated of its supernatant. Then a fresh plating medium is added to the cell pellet to prepare a cell suspension. (Step E-1)

Here, plating mediums such as 'iCells, R1057' from Fujifilm Cellular Dynamics, Inc. may be used without being limited thereto, but other mediums known to be usable in the differentiation and culture of cardiomyocytes can be also used.

Preferably, Nexel Cardiosight®-S Media which includes RPMI1640 and B27 supplement without vitamin A is used as the plating medium.

In addition, the human stem cell-derived cardiomyocytes prepared in step S110 are taken out of the liquid nitrogen tank and thawed in the water bath set at temperature of 37° C. Then the cell solution is diluted into the plating medium in a dropwise manner. Lastly, the solution containing the cells are placed into the centrifuge and centrifuged for 3 minutes at 180 g.

Specifically, the thawed cell solution is added dropwise to 8 ml of the plating medium, and the inside of the cell vial is washed with 1 ml of plating medium to harvest the remaining cells. Cardiomyocytes are suspended in a total of 10 ml of plating medium and centrifuged.

Following centrifugation, the supernatant is discarded, and the cell pellet is dissolved in 1 ml of fresh plating medium to prepare a cell suspension solution.

Thereafter, in step E-2, the cell suspension solution prepared in step E-1 is seeded onto wells of the MEA plate at a cell count of $5 \times 10^4$, ensuring that all dots of the electrodes are covered, after the removal of fibronectin solution.

In this process, the fibronectin solution added to wells of the MEA plate is completely removed, and $5 \times 10^4$ human stem cell-derived cardiomyocytes, most preferably, are seeded onto wells of the MEA plates so as to cover all dots of electrodes.

If possible, 10 μl of 1 ml cell suspension is taken to be mixed with 10 μl of trypan blue for cell counting. After counting, the appropriate volume from the 1 ml cell suspension is taken for the respective number of wells to be seeded and centrifuged, then the supernatant is aspirated. Lastly, 5 μl of cells per well are seeded.

(6) Second Incubation Step <S160, Step (F)>

In this step (S160), the predetermined amount of plating medium is added to wells of the MEA plate that had human stem cell-derived cardiomyocytes seeded in step S150 and is further incubated in the cell culture incubator.

Specifically, the second incubation step is comprised of three incubation processes which are performed under different incubation conditions. First, after step E-2, where human stem cell-derived cardiomyocytes are seeded into wells of the MEA plates, ensuring to cover all dots of electrodes, the MEA plate is incubated at room temperature (20° C. to 25° C.) for 60 minutes (Step F-1).

This process allows the human stem cell-derived cardiomyocytes seeded to cover all dots of electrodes to better adhere to the center of the well.

Next, step F-2 adds additional plating medium to wells of the MEA plate that have undergone the first incubation (step F-1) and place the MEA plate into the cell culture incubator for the second incubation at 37° C. and 5% $CO_2$ for 23 to 24 hours (preferably 1 day).

Lastly, step F-3 replaces the plating medium added to wells of the MEA plate that have undergone the second incubation (step F-2) with maintenance medium and place the MEA plate into the cell culture incubator for the third incubation at 37° C. and 5% $CO_2$ for 6 to 7 days (preferably 6 days).

Here, media such as Nexel Cardiosight®-S media (maintenance medium) or RPMI1640 (11875093) can be used as maintenance medium, but other mediums known to be usable in differentiation and culture of cardiomyocytes can be also used.

As a result, the first to third incubation processes in the second incubation step (S160) are most preferred to be carried over a span of 7 days, and the third incubation step (step F-3) requires the medium added in the MEA plate to be replaced with a fresh maintenance medium at a 2-day interval over 7 days.

Figure 5:
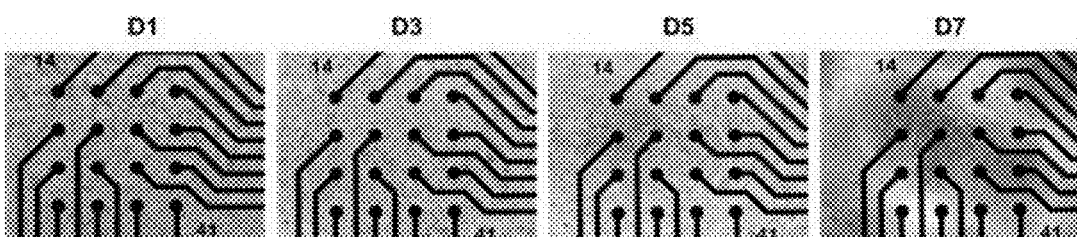
FIG. 5 depicts photographs showing the results of observing time-dependent changes in the state of human stem cell-derived cardiomyocytes seeded on electrodes disposed in each well of an MEA plate which is used in an MEA plate preparation step in the method of assessing drug cardiac safety using human stem cell-derived cardiomyocytes according to the present invention.

It can be confirmed that cardiomyocytes places on the electrodes agglomerate and beat with increasing intensity as it progresses through the first to third incubation processes of the 7-day second incubation step (S160), as visualized in FIG. 5.

(7) Cardiac Safety Assessment Step <S170, Step (G)>

This step (S170) is comprised of measuring changes in measurement values of beat rate, spike amplitude, and field potential duration depending on the administrated concentration of the drug to be assessed into wells of the MEA plate, which has been seeded with the human stem cell-derived cardiomyocytes, through the use of MEA measurement device connected to the electrodes in each well, and assessing cardiac safety of the drug based on the measured values.

More specifically, the cardiac safety assessment step is subdivided into multiple steps. First, step G-1, replaces the maintenance medium in the MEA plate that has undergone the 3rd incubation step (step F-3) with a fresh maintenance medium, and places the MEA plate into the cell culture incubator at 37° C. and 5% $CO_2$ for 3 to 5 hours (preferably 3 hours) for stabilization of cells.

Next, the first set of measurement values on beat rate, spike amplitude, and field potential duration of the human stem cell-derived cardiomyocytes are taken (step G-2) with the MEA measurement device for the MEA plate that has undergone cell stabilization step (step G-1).

The first set of measurement values taken through the MEA measurement device is a baseline value with no drugs administered to the cells, which is a portion of multiple parameters that serve as the basis for the drug cardiac safety assessment.

Here, it is preferable to have pipetting done for all wells and go through a stabilization process of 10 minutes before the baseline measurements. The measurement should be recorded over the span of 5 minutes.

After the completion of the first measurement, a portion of the maintenance medium, which corresponds to $\frac{1}{10}$ of the total volume in the well, is removed from wells of the MEA plate that has undergone the stabilization process. (Step G-1)

Then a predetermined concentration of the drug to be assessed is added to the same volume of maintenance medium that has been removed from the well immediately. After 30 to 40 minutes (preferably 30 minutes), second measurement values on beat rate, spike amplitude, and field potential duration of the human stem cell-derived cardiomyocytes are taken through the MEA measurement device. (Step G-3)

The second measurement value taken through the MEA measurement device is a treatment value with the administration of predetermined drug concentration, which is a portion of multiple parameters that serve as the basis for the drug cardiac safety assessment.

Therefore, it is preferable to repeat the second measurement step (Step G-3) at least twice with differing drug concentrations to generate two or more sets of second measurement values.

Furthermore, in the second measurement step (G-3), it is preferable that values are measured after 30 minutes of drug administration, with differing drug concentrations per measurement set.

For example, after each well was treated with drug-to-be-assessed at 10x for the initial measurement set, the second measurement step (step G-3) is repeated with gradually increasing the concentration of the drug to generate multiple sets of second measurement values.

Finally, Step G-4 uses first and second measurement (at least two sets) values gathered on the step G-2 and G-3 to assess the cardiac safety of the drug through changes in the pattern of FPDcF (field potential duration corrected by Fridericia's formula) and Spike amplitude using the MEA measurement device.

Here, raw files stored in the MEA measurement device program are loaded, and the desired section of the data is re-recorded and saved as a CSV file. Then the drug's effect on the field potential of cardiomyocytes is evaluated by the changes in the reaction parameter, based on the first and second measurement values which include beat interval, spike amplitude, and field potential duration, to various concentrations of the drug.

Figure 6:
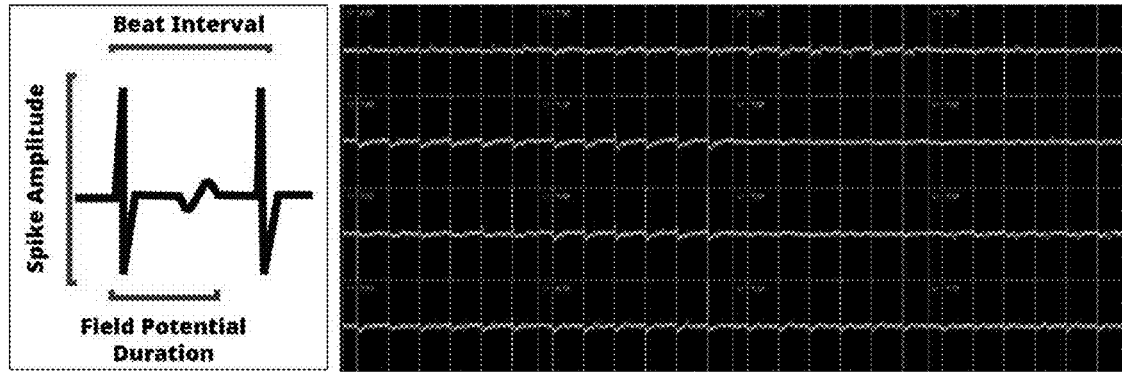
FIG. 6 is a graph showing the results of extracting measurement information about human stem cell-derived cardiomyocytes, seeded in each well, through electrodes disposed in each well of an MEA plate in a drug cardiac assessment step in the method of assessing drug cardiac safety using human stem cell-derived cardiomyocytes according to the present invention.

In specific, if an MEA plate with 16 electrodes, as shown in FIG. 6, is used, then the beat and field potential recorded from 16 electrodes in each well can be seen simultaneously. In the schematics of beat and field potential from the left side of FIG. 6, it can be deduced that beat interval, spike amplitude, and field potential duration are analyzed and utilized as parameter measurement values.

Here, the field potential duration (FPD) is an analogue to the QT interval, and like QT interval, it changes according to the beat. Therefore, to properly interpret the direct effect on the FPD or the QT, it is crucial to calculate and correct the change in the beat ratio into field potential duration corrected by Fridericia's formula (FPDcF). In addition, the cardiac toxicity of a drug can be determined through changes in FPDcF and spike amplitude.

Therefore, the FPDcF (field potential duration corrected by Fridericia's formula) value is derived by using Fridericia's formula, defined as "FPDcF=Field Potential Duration/ Beat Rate (Interval)$\frac{1}{3}$".

Figure 7:
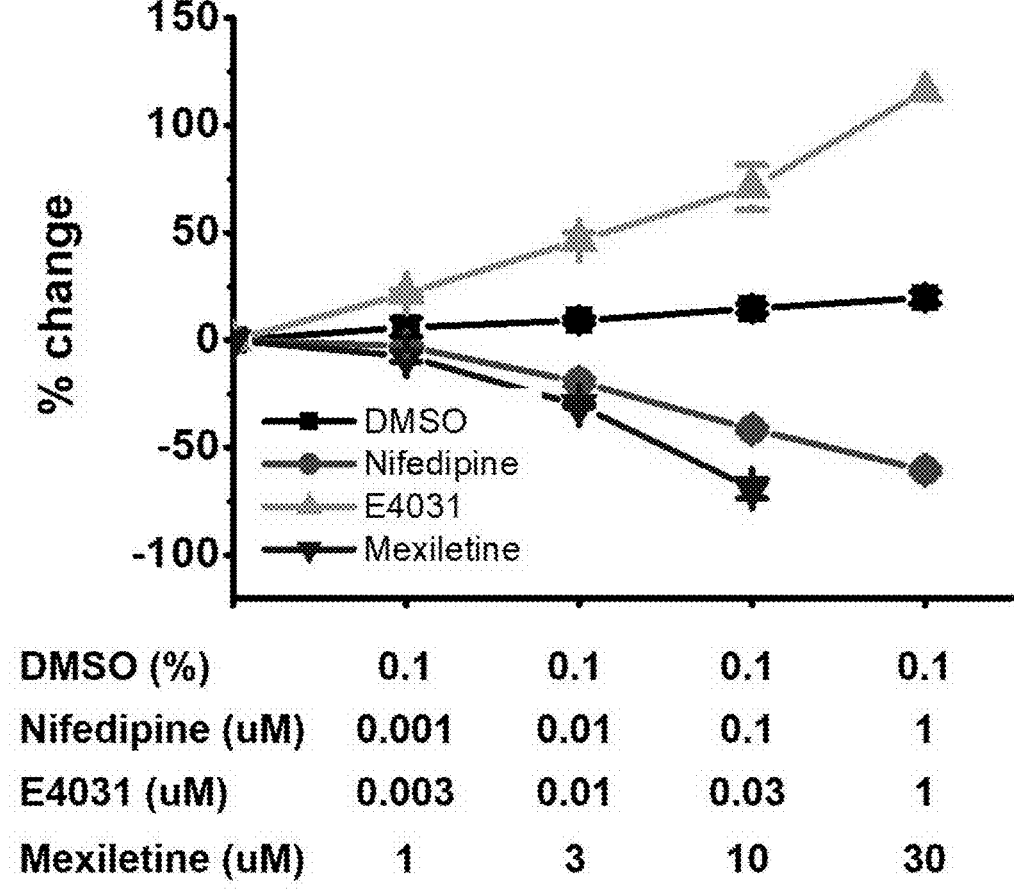
FIG. 7 is a graph showing the results of assessing change patterns in FPDcF (field potential duration corrected by Fridericia's formula) and spike amplitude depending on changes in the concentration of each drug in a drug cardiac safety assessment step in the method of assessing drug cardiac safety using human stem cell-derived cardiomyocytes according to the present invention.

As a practical example, FIG. 7 displays the cardiac safety assessment results when representative ion channel inhibitors (Calcium channel blocker—Nifedipine, potassium channel blocker—E4031, and sodium channel blocker Mexiletine) are administered to human stem cell-derived cardiomyocytes according to the present invention.

In FIG. 7, changes in FPDcF and spike amplitude values can be seen when the human stem cell-derived cardiomyocytes are exposed to various concentrations of ion channel blockers. While there were no changes in the FPDcF value when cells were treated with DMSO (negative control), FPDcF values were increasing or decreasing depending on the administered concentrations of Nifedipine and E4031. On the other hand, groups treated with Mexiletine exhibited a decrease in the spike amplitude according to the drug concentration.

Most preferably, Step G-4, where the evaluation of the drug cardiac safety using changes in FPDcF and spike amplitude depending on the drug concentration using MEA measurement device, bases its criteria on the literature of 'Gintant, G et al., Regul Toxicol Pharmacol. 2020 Aug. 19; 117: 104756.', where it states, "as a result of the CiPA study, when FDPcF, which is changed by the drug, changes by 20% or more (n=3), it is significant and the degree of drug cardiac safety can be distinguished". Furthermore, step G-4 may be designed to generate output data based on the above criteria.

Therefore, drug cardiac safety assessment using human stem cell-derived cardiomyocytes according to the present invention overcomes shortcomings of the hERG assay currently used to assess the cardiotoxicity of drugs in the preclinical stage for new drug development and presents a method capable of assessing cardiotoxicity of drugs in vitro in a more accurate and integrated manner.

The embodiments disclosed in the present invention are not intended to limit the technical spirit of the present invention, but are intended to describe the invention, and the scope of the technical spirit of the present invention is not limited by these embodiments. The scope of protection should be construed by the appended claims, and all technical ideas within the scope equivalent thereto should be construed as being falling within the scope of the present invention.

The invention claimed is:

1. A method of assessing drug cardiac safety using human stem cell-derived cardiomyocytes, the method comprising:

step (A) of preparing cardiomyocytes by culturing human stem cells to differentiate into cardiomyocytes;

step (B) of diluting fibronectin in phosphate buffered saline (PBS) to a concentration of 50 µg/ml, wherein the step (B) comprises:

step (B-1) of preparing a fibronectin stock by dissolving fibronectin in the PBS at a concentration of 1 mg/ml, and step (B-2) of diluting the fibronectin prepared in the step (B-1) in the PBS to a concentration of 50 µg/ml;

step (C) of adding the fibronectin solution obtained in the step (B-2) so as to cover all dots of electrodes disposed in a center of each of a plurality of wells arranged in a multielectrode array (MEA) plate, and adding the PBS to spaces between the wells of the MEA plate to fill the spaces;

step (D) of placing the MEA plate, to which the fibronectin solution and the PBS have been added through the step (C), in a cell incubator maintained at 37° C. under 5% $CO_2$ for 50-60 minutes to coat the wells;

step (E) of removing the fibronectin solution from specific wells of the MEA plate coated in the step (D), and then seeding the cardiomyocytes prepared in the step (A) in the specific wells so as to cover all dots of the electrodes, wherein the step (E) comprises:

step (E-1) of adding the human stem cell-derived cardiomyocytes prepared in the step (A) to a plating medium, centrifuging the mixture, removing the natant and adding fresh plating medium to prepare a cell suspension; and step (E-2) of removing the fibronectin solution from each of the specific wells of the MEA plate and seeding, in each specific well, a portion of the cell suspension prepared in the step (E-1) containing $5 \times 10^4$ human stem cell-derived cardiomyocytes, so as to cover all dots of the electrodes;

step (F) of adding a predetermined medium to the specific wells of the MEA plate that have been seeded with the cardiomyocytes through the step (E), and then incubating the MEA plate in a cell incubator, wherein the step (F) comprises:

step (F-1) of incubating the MEA plate, seeded with the cardiomyocytes in the step (F-2), at 20° C. to 25° C. for 60 minutes as a first incubation;

step (F-2) of after the first incubation of the step (F-1) is complete, adding a plating medium to each of the specific wells and then placing the MEA plate in a cell culture incubator maintained at 37° C. under 5% $CO_2$ for 23-24 hours as a second incubation; and step (F-3) of after the second incubation of the step (F-2) is complete, replacing the plating medium in each of the specific wells with a maintenance medium, and then incubating the MEA plate at 37° C. under 5% $CO_2$ for 6-7 days as a third incubation;

step (G) of measuring changes in information values for beat rate, spike amplitude, and field potential duration in the specific wells of the MEA plate, which have been seeded with the cardiomyocytes and incubated for a predetermined period in the step (F), depending on whether a drug to be assessed has been added and on the concentration of the added drug, by using a multi-electrode array (MEA) measurement device electrically connected to the electrodes disposed in each well of the MEA plate, and assessing the cardiac safety of the drug based on the measured information values; and step (H) of providing an application of the measurement data by transmitting the measured information values and the results of the cardiac safety assessment from the step (G) to a drug evaluation system for further analysis of the drug's safety.

2. The method according to claim 1, wherein the human stem cells differentiated into cardiomyocytes in the step (A) are selected from human pluripotent stem cells (hPSCs) and human embryonic stem cells (hESCs).

3. The method according to claim 1, wherein in step the (F-3) the maintenance medium is replaced with fresh maintenance medium at two day intervals during the third incubation.

4. The method according to claim 1, wherein the step (G) comprises:

step (G-1) of replacing the maintenance medium in each of the specific wells of the MEA plate, after completion of the third incubation in the step (F-3), with fresh maintenance medium, and placing the MEA plate in a cell incubator at 37° C. under 5% $CO_2$ for 3-5 hours to stabilize the cardiomyocytes;

step (G-2) of generating first measurement information by measuring values of beat rate, spike amplitude, and field potential duration for the cardiomyocytes in at least one of the specific wells after cell stabilization in the step (G-1) using the MEA measurement device, wherein the first measurement information represents baseline values with no drug added;

step (G-3) of removing a portion of the maintenance medium, corresponding to about one-tenth of the total volume, from at least one of the specific wells after stabilization in the step (G-1); adding the drug to be assessed at a predetermined concentration in an amount equal to the removed portion; after 30-40 minutes, generating second measurement information by measuring values of best beat rate, spike amplitude, and field potential duration for the cardiomyocytes in said well using the MEA measurement device, wherein the step (G-3) is repeated at least twice with different concentrations of the drug to obtain multiple sets of second measurement information; and step (G-4) of determining the cardiac safety of the drug based on changes in field potential duration corrected by Fridericia's formula (FPDcF) and in spike amplitude as a function of the drug concentration using the first measurement information from the step (G-2) and the at least;

two sets of second measurement information from the step (G-3).

* * * * *